United States Patent [19]

Saito et al.

[11] 4,235,891

[45] Nov. 25, 1980

[54] COMBATING PESTS WITH O-ALKYL-S-ALKYL-O-HALOALKYL-PHOSPHATES

[75] Inventors: Junichi Saito, Tokyo; Akio Kudamatsu, Kanagawa; Toyohiko Kume; Shinichi Tsuboi, both of Tokyo, all of Japan

[73] Assignee: Nihon Tokusho Noyaku Seizo K.K., Tokyo, Japan

[21] Appl. No.: 52,632

[22] Filed: Jun. 27, 1979

[30] Foreign Application Priority Data

Jul. 5, 1978 [JP] Japan .................................. 53-80934

[51] Int. Cl.$^3$ ........................ A01N 57/10; C07F 9/165
[52] U.S. Cl. .................................. 424/224; 260/955; 260/963
[58] Field of Search .................. 260/955, 963; 424/224

[56] References Cited

FOREIGN PATENT DOCUMENTS 107581 8/1974 German Democratic Rep. ..... 260/963
51-101131 9/1976 Japan ........................................ 260/963
51-101132 9/1976 Japan ........................................ 260/963

*Primary Examiner*—Anton H. Sutto
*Attorney, Agent, or Firm*—Sprung, Felfe, Horn, Lynch & Kramer

[57] ABSTRACT

O-alkyl-S-alkyl-O-haloalkyl-phosphates of the formula

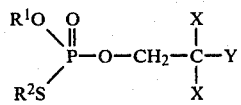

in which
$R^1$ and $R^2$ each independently is alkyl with 1–4 carbon atoms,
X is halogen, and
Y is halogenoalkyl with 1–4 carbon atoms,
which possess arthropodicidal and nematicidal properties.

10 Claims, No Drawings

COMBATING PESTS WITH O-ALKYL-S-ALKYL-O-HALOALKYL-PHOSPHATES

The present invention relates to and has for its objects the provision of particular new O-alkyl-S-alkyl-O-haloalkyl-phosphates which possess arthropidical and nematicidal properties, active compositions in the form of mixtures of such compounds with solid and liquid dispersible carrier vehicles, and methods for producing such compounds and for using such compounds in a new way, especially for combating pests, e.g. insects, acarids and nematodes, with other and further objects becoming apparent from a study of the within specification and accompanying examples.

Japanese Laid-open Patent Application No. 51-101131 discloses that the organic phosphate derivatives having the formula

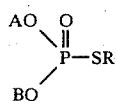   (IV), wherein

R represents lower alkyl,

A represents lower alkyl, cycloalkyl or haloalkyl and

B represents lower alkyl or haloalkyl, provided that when A and B both represent lower alkyl, A and B are different from each other, have fungicidal activity when employed by water-surface application.

Japanese Laid-open Patent Application No. 51-101132 discloses that the organic phosphate derivatives having the formula

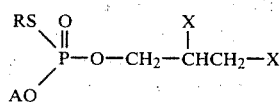   (V), wherein

R represents lower alkyl,

A represents lower alkyl, and

X represents a halogen atom, have fungicidal activity.

Furthermore, East German Pat. No. 107,581 discloses that the organic phosphate derivatives having the formula

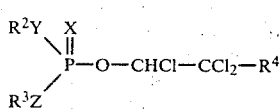   (VI), wherein $R^4$ represents a chlorine atom or monochloromethyl, $R^2$ represents alkyl, $R^3$ represents alkyl and X, Y and Z each represent oxygen or sulfur, have insecticidal and acaricidal activities.

The present invention now provides, as new compounds, the organic phosphate derivatives of the general formula

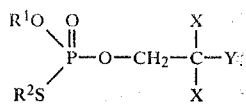   (I)

in which $R^1$ represents alkyl with 1–4 carbon atoms, $R^2$ represents alkyl with 1–4 carbon atoms, X represents halogen and Y represents halogenoalkyl with 1–4 carbon atoms.

These novel compounds exhibit excellent insecticidal, acaricidal and nematicidal activities; moreover, they are fast-acting and are active via the vapor phase. Their pesticidal activity is, surprisingly, superior to that of the compounds of the prior art mentioned above.

In formula (I), $R^1$ and $R^2$ may each represent methyl, ethyl, n- or isopropyl or n-, iso-, sec.- or tert.-butyl and X may represent fluorine, chlorine, bromine or iodine. Examples of the radicals Y are mono- (di- or tri-)fluoro-(chloro-, bromo- or iodo-)methyl, 1-(or 2-) fluoro-(chloro-, bromo- or iodo-)ethyl, 1,1-(1,2- or 2,2-) difluoro-(chloro-, bromo- or iodo-)ethyl and 1,1,2-(1,2,2- or 2,2,2,-) tri- fluoro-(chloro-, bromo- or iodo-)ethyl.

Preferably, $R^1$ represents ethyl, $R^2$ represents n-propyl and Y represents di- or trihalogenomethyl.

The invention also provides a process for the preparation of a compound of the formula (I) in which (a) a thiophosphoryl halide of the general formula

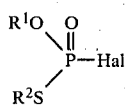   (II), in which $R^1$ and $R^2$ have the meanings stated above and Hal represents halogen, is reacted with a halogenoalcohol, or salt thereof, of the general formula

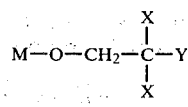   (III), in which

X and Y have the meanings stated above and

M represents hydrogen or an alkali metal, or (b) a thiophosphoryl halide of the general formula

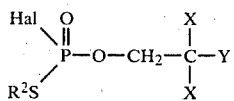   (VII), in which $R^2$, X and Y have the meanings stated above and

Hal represents halogen, is reacted with an alcohol or alcoholate of the general formula

   (VIII), in which $R^1$ has the meaning stated above and

M represents hydrogen or an alkali metal, or (c) a phosphite of the general formula $$\begin{array}{c} R^1O \\ \phantom{Y-}\diagdown \\ \phantom{Y-C-CH_2-O}P-OH \\ \phantom{Y-}\diagup \\ Y-\underset{\underset{X}{|}}{\overset{\overset{X}{|}}{C}}-CH_2-O \end{array} \quad (IX),$$

in which
R$^1$, X and Y have the meanings stated above,
is reacted with a sulphenyl halide of the general formula $$R^2S-Hal \quad (X),$$

in which
R$^2$ has the meaning stated above and
Hal represents halogen.

Examples of the compounds (II), to be used as starting materials in process variant (a), are O-ethyl-S-n-propyl phosphoro chloride thioate and the corresponding bromide.

Examples of the compounds (III), also to be used as starting materials in process variant (a), are 2,2,3,3-tetrafluoro-1-propanol and 2,2,3,3,3-pentafluoro-1-propanol, as well as their sodium and potassium salts.

When O-ethyl-S-n-propyl phosphoro chloride thioate and 2,2,3,3,-tetrafluoro-1-propanol are used as starting materials, the reaction can be represented by the following equation:

$$\begin{array}{c} C_2H_5O \phantom{xx} O \\ \diagdown \phantom{x} \| \\ \phantom{CH_3CH_2CH_2S}P-Cl + HO-CH_2CF_2CHF_2 \longrightarrow \\ \diagup \\ CH_3CH_2CH_2S \end{array}$$

$$\begin{array}{c} C_2H_5O \phantom{xx} O \\ \diagdown \phantom{x} \| \\ \phantom{CH_3CH_2CH_2S}P-O-CH_2CF_2CHF_2 + HCl \\ \diagup \\ CH_3CH_2CH_2S \end{array}$$

Examples of the compounds (VII), to be used as starting materials in process variant (b), are O-2,2,3,3-tetrafluoro-1-propyl-S-n-propylphosphoro chloride thioate and O-2,2,3,3,3-pentafluoro-1-propyl-S-n-propyl phosphoro chloride thioate, as well as the corresponding bromides.

An example of the other starting material, of the formula (VIII), is ethanol. The sodium or potassium salt of this alcohol can also be used.

When O-2,2,3,3,3-pentafluoro-1-propyl-S-n-propyl phosphoro chloride thioate and ethanol are employed as starting materials, the reaction can be represented by the following equation:

$$\begin{array}{c} Cl \phantom{xx} O \\ \diagdown \phantom{x} \| \\ \phantom{CH_3CH_2CH_2S}P-O-CH_2CF_2CF_3 + C_2H_5OH \longrightarrow \\ \diagup \\ CH_3CH_2CH_2S \end{array}$$

$$\begin{array}{c} C_2H_5O \phantom{xx} O \\ \diagdown \phantom{x} \| \\ \phantom{CH_3CH_2CH_2S}P-O-CH_2CF_2CF_3 + HCl \\ \diagup \\ CH_3CH_2CH_2S \end{array}$$

Especially when M in the formula (III) or (VIII) represents hydrogen, process variant (a) or (b) according to this invention can be carried out in the presence of an acid-binding agent. Examples of suitable acid-binding agents are the commonly employed hydroxides, carbonates, bicarbonates and alcoholates of the alkali metals, and tertiary amines such as triethylamine, diethylaniline or pyridine.

An acid-binding agent can also be used in variant (c).

Alternatively, instead of carrying out the process in the presence of an acid-binding agent, a salt of the halogenoalcohol (III) or alcohol (VIII), in particular an alkali metal salt thereof, can be employed in the reaction according to variant (a) or (b).

Examples of the compounds of the formula (IX), used as starting materials in process variant (c), are O-ethyl-O-2,2,3,3-tetrafluoro-1-propyl phosphite and O-ethyl-O-2,2,3,3,3-pentafluoro-1-propyl phosphite.

Examples of the other starting materials, of the formula (X), are 1-propane sulphenyl chloride and 1-propane sulphenyl bromide.

Each sulphenyl chloride or bromide used herein can easily be synthesized by reacting the corresponding disulfide with chlorine, bromine, sulfuryl chloride or sulfuryl bromide.

When O-ethyl-O-2,2,3,3,3-pentafluoro-1-propyl phosphite and 1-propane sulphenyl chloride are used as starting materials, the reaction can be represented by the following equation:

$$\begin{array}{c} C_2H_5O \\ \diagdown \\ \phantom{CF_3CF_2CH_2O}P-OH + CH_3CH_2CH_2SCl \longrightarrow \\ \diagup \\ CF_3CF_2CH_2O \end{array}$$

$$\begin{array}{c} C_2H_5O \phantom{xx} O \\ \diagdown \phantom{x} \| \\ \phantom{CH_3CH_2CH_2S}P-O-CH_2CF_2CF_3 + HCl \\ \diagup \\ CH_3CH_2CH_2S \end{array}$$

The process of the present invention, whether variant (a), (b) or (c), is carried out preferably in the presence of a solvent or diluent. For this purpose, any inert solvent or diluent may be employed.

Examples of such solvents and diluents are water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene or chlorobenzene; ethers such as diethyl ether, methyl ethyl ether, di-isopropyl ether, dibutyl ether, propylene oxide, dioxane or tetrahydrofuran; ketones such as acetone, methyl ethyl ketone, methyl iso-propyl ketone or methyl iso-butyl ketone; nitriles such as acetonitrile, propionitrile or acrylonitrile; alcohols such as methanol, ethanol, iso-propanol, butanols or ethylene glycol; esters such as ethyl acetate or amyl acetate; amides such as dimethylformamide or dimethylacetamide; sulfones and sulfoxides such as dimethylsulfoxide and sulfolane; and organic bases such as pyridine.

The process of the present invention, whether variant (a), (b) or (c), can be carried out over a wide range of temperatures. Generally, it is carried out at a temperature of from −20° C. to the boiling point of the reaction mixture, preferably from 0° to 100° C. The reaction pressure is preferably normal pressure, although elevated or reduced pressure can be employed.

As already mentioned, the compounds according to the present invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine, since they are also active against animal parasites, in particular ectoparasites such as parasitic fly larvae and ticks.

The active compounds are well tolerated by plants, have a favorable level of toxicity to warm-blooded animals, and can be used for combating arthropod pests, especially insects, and nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia keuhniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 per cent by weight of active compound, preferably from 0.5 to 90 per cent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0001 to 20% by weight of active compound, preferably from 0.005 to 10% by weight. With certain methods of application, for example the ultra-low volume process, the concentrations of active compound can be higher (up to 95%, or even 100%).

The compounds may be employed in a customary manner appropriate for the particular use forms.

The active compounds according to the invention can be present in the formulations, or in the various use forms, as a mixture with other active compounds, such as fungicides, insecticides, acaricides, nematicides, herbicides, bird repellents, growth factors, plant nutrients and agents for improving soil structure.

In general, 0.03 to 10 kg, preferably 0.3 to 6 kg, of active compound are employed per hectare of soil surface.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The following preparative Examples are given to illustrate the process for producing the compounds of this invention.

EXAMPLE 1

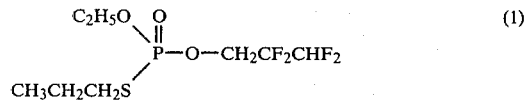

(1)

To a mixture of 6.1 g of O-ethyl-S-n-propylphosphoro chloride thioate, 4 g of 2,2,3,3-tetrafluoro-1-propanol and 30 ml of toluene there were added dropwise 3.1 g of triethylamine with stirring at 0°-5° C. After this addition, the temperature was gradually raised to 60° C. at which temperature stirring was continued for 2 hours.

After cooling, the mixture was washed successively with 1% aqueous hydrochloric acid, 2% aqueous potassium hydroxide and water, dried over sodium sulfate anhydride, evaporated to remove toluene and distilled under reduced pressure to yield 6.4 g of the desired product, O-ethyl-S-n-propyl-O-2,2,3,3-tetrafluoro-1-propylphosphorothiolate (b.p.=105°-108° C./1.5 mm Hg; $n_D^{20}=1.4155$).

EXAMPLE 2

The following compound was produced in a manner analogous to that described in Example 1.

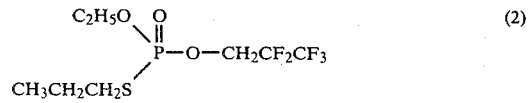

(2)

O-ethyl-S-n-propyl-O-2,2,3,3,3-pentafluoro-1-propyl-phosphoro thiolate.

Various pesticidal compositions according to this invention are described in the following examples. The compounds of the present invention are each identified by the number of the corresponding preparative example. Parts are by weight.

EXAMPLE 3

A wettable powder was prepared by pulverizing and mixing 15 parts of compound No. 1, 80 parts of a mixture (1:5) of diatomaceous earth and kaolin, and 5 parts of an emulsifier (a polyoxyethylene alkylphenyl ether). This could be diluted with water to a concentration of 0.05% before application by spraying.

EXAMPLE 4

An emulsifiable concentrate was prepared by mixing and stirring 30 parts of compound No. 2, 30 parts of xylene, 30 parts of methylnaphthalene and 10 parts of a polyoxyethylene alkylphenyl ether. This could be diluted with water to a concentration of 0.05% before spraying.

EXAMPLE 5

A dusting agent was prepared by pulverizing and mixing 2 parts of compound No. 1 and 98 parts of a mixture (1:3) of talc and clay. This could be applied by scattering.

EXAMPLE 6

A dusting agent was prepared by pulverizing and mixing 1.5 parts of compound No. 2, 0.5 part of isopropyl hydrogen phosphate (PAP), and 98 parts of a mixture (1:3) of talc and clay.

EXAMPLE 7

10 parts of compound No. 1, 10 parts of bentonite, 78 parts of a mixture (1:3) of talc and clay, and 2 parts of lignin sulfonate were mixed. 25 parts of water were added to the mixture. The whole was mixed thoroughly and then processed with an extrusion granulator into granules of 20 to 40 mesh, which were dried at 40°–50° C.

EXAMPLE 8

95 parts of clay powder having a particle size distribution of 0.2 to 2 mm were placed in a rotary mixer. During rotation, there was sprayed over the particles a solution of 5 parts of compound No. 2 in an organic solvent thereby wetting them uniformly. Then, drying at 40° to 50° C. was effected in order to form coated granules.

EXAMPLE 9

An oil preparation was prepared by mixing and stirring 0.5 part of compound No. 1, 20 parts of a mixture of highboiling aromatic compounds and 79.5 parts of kerosine.

The insecticidal, acaricidal and nematicidal activity of the compounds of this invention is illustrated by the following biotest examples.

In these examples, the compounds according to the present invention are each identified by the number (given in brackets) from the corresponding preparative example, hereinabove.

The known comparison compounds are identified as follows:

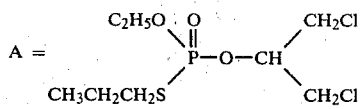

(a compound disclosed in Japanese Laid-open Patent Application No. 51-101131)

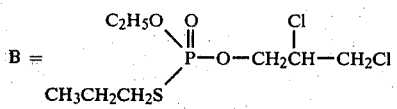

(a compound disclosed in Japanese Laid-open Patent Application No. 51-101132)

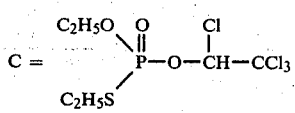

(a compound disclosed in East German Pat. No. 107,581)

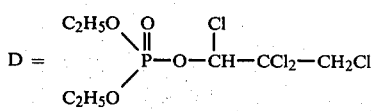

(a compound disclosed in East German Pat. No. 107,581).

EXAMPLE 10

Test on larvae of *Spodoptera litura:*

Solvent: xylene, 3 parts by weight
Emulsifier: polyoxyethylene alkylphenyl ether, 1 part by weight To form a suitable preparation of an active compound, 1 part by weight of the active compound was mixed with the above amount of the solvent containing the above amount of the emulsifier, and the mixture was diluted with water to a predetermined concentration.

Sweet-potato leaves were dipped in an aqueous formulation containing a predetermined concentration of the active compound. After drying the leaves in air, they were placed in a Petri dish 9 cm in diameter. Then, 10 third-instar larvae of *Spodoptera litura* were released into the Petri dish. The dish was placed in a constant-temperature chamber at 28° C. Twenty-four hours later, the number of dead larvae were examined, and the killing rate was calculated. The results are shown in Table 1.

TABLE 1

| Compound | Killing rate (%) at a concentration of the active ingredient of 1000 ppm |
|---|---|
| (1) | 100 |
| (2) | 100 |
| A | 0 |
| B | 20 |
| C | 0 |
| D | 0 |

EXAMPLE 11

Test on *Callosobruchus chinensis*

A filter paper was spread in a Petri dish having a diameter of 9 cm. One milliliter of an aqueous formulation containing a predetermined concentration of the active compound (the formulation having been prepared as in Example 10) was placed in the dish. Twenty specimens of *Callosobruchus chinensis* were placed in the Petri dish, and the dish was put into a constant-temperature chamber at 28° C. After 24 hours the killing rate was determined.

The results are shown in Table 2.

TABLE 2

| Compound | Killing rate (%) at a concentration of the active ingredient of | |
|---|---|---|
| | 1000 | 10 ppm |
| (1) | 100 | 100 |
| (2) | 100 | 100 |
| A | 100 | 0 |
| B | 100 | 0 |
| C | 100 | 0 |
| D | 100 | 0 |

EXAMPLE 12

Test on *Nephotettix cincticeps* having resistance to organophosphorus preparations Rice plants each about 10 cm in height were planted in pots each 12 cm in diameter. Onto the rice plants was applied an aqueous preparation containing a predetermined concentration of the active compound (the formulation having been prepared as in Example 10) at a rate of 10 ml per pot. After drying the applied preparation, the pots were capped with wire-gauze cages each 7 cm in diameter and 14 cm in height, into which 30 female imagos of *Nephotettix cincticeps* having resistance to organophosphorus agents were released. The pots were then placed in a constant-temperature chamber. Twenty-four hours later, the numbers of dead insects were examined, and the killing rate was calculated. The results are shown in Table 3.

TABLE 3

| Compound | Killing rate (%) at a concentration of the active ingredient of | |
|---|---|---|
| | 1000 | 100 ppm |
| (1) | 100 | 100 |
| (2) | 100 | 100 |
| A | 100 | 0 |
| B | 70 | 0 |
| C | 100 | 0 |
| D | 0 | 0 |

EXAMPLE 13

Test on *Musca domestica*

A filter paper was laid on the bottom of a Petri dish 9 cm in diameter, to which was added 1 ml of the aqueous preparation of the active compound diluted to a prescribed concentration and which had been prepared as in Example 10. Ten female *Musca domestica* imagos were placed in the dish. The dish was kept in a constant-temperature room at 28° C. After 24 hours, the number of the killed insects was counted and the killing rate was calculated.

The results are shown in Table 4 below.

TABLE 4

| Compound | Killing rate (%) at a concentration of the active ingredient of | |
|---|---|---|
| | 1000 | 100 ppm |
| (1) | 100 | 100 |
| (2) | 100 | 100 |
| A | 100 | 0 |
| B | 100 | 0 |
| C | 100 | 0 |
| D | 60 | 0 |

EXAMPLE 14

Test on *Tetranychus telarius* (Spray test)

Kidney bean leaves at the first leaf-extension stage cultivated in a pot 6 cm in diameter were infested with 50–100 *Tetranychus telarius* imagos which had acquired resistance to commercially available organic phosphate agents. Two days later, an aqueous preparation of the active compound diluted to the prescribed concentration and which had been prepared as in Example 10 was sprayed in an amount of 40 ml per pot. After ten days in a greenhouse, the control effect was assessed and rated by indices. The indices used are as follows:

3: surviving imagos—0%
2: surviving imagos—more than 0% and less than 5% based on the untreated case.
1: surviving imagos—from 5% to 50% based on the untreated case.
0: surviving imagos—more than 50% based on the untreated case.

The results are shown in Table 5 below.

TABLE 5

| Compound | Control value at a concentration of the active compound of | |
|---|---|---|
| | 1000 | 100 ppm |
| (1) | 3 | 3 |
| (2) | 3 | 3 |
| A | 0 | 0 |
| B | 2 | 0 |
| C | 0 | 0 |
| D | 0 | 0 |

EXAMPLE 15

Test on *Culex pipiens*

Test Method

Into a high Petri dish 9 cm in diameter there were poured 100 ml of the aqueous preparation of the active compound diluted to the prescribed concentration and which had been prepared as in Example 10. Twenty-five fourth-instar larvae of *Culex pipiens* were placed in the dish, which was then put in a constant temperature room at 28° C. After 24 hours, the number of the killed larvae was counted and the killing rate was calculated.

The results are shown in Table 6 below.

TABLE 6

| Compound | Killing rate (%) at a concentration of the active ingredient of | |
|---|---|---|
| | 1 | 0.1 ppm |
| (1) | 100 | 100 |
| (2) | 100 | 100 |
| A | 0 | 0 |

TABLE 6-continued

| Compound | Killing rate (%) at a concentration of the active ingredient of | |
|---|---|---|
| | 1 | 0.1 ppm |
| B | 100 | 0 |
| C | 0 | 0 |
| D | 0 | 0 |

EXAMPLE 16

Test on *Meloidogyne incognita acrita*

An active-compound preparation was prepared by pulverizing and mixing 2 parts by weight of the active compound and 98 parts by weight of talc.

The active compound, processed as above, was added to soil infested by *Meloidogyne incognita acrita* in such amounts as to provide a concentration of 50 ppm, 25 ppm 10 ppm and 5 ppm, respectively. The soil and active compound were mixed uniformly by stirring and then charged into pots each of 0.0002 are. In the treated soil were sown about 20 seeds of tomato (variety: KURIHARA) per pot. The tomato seeds were cultivated in a greenhouse. Four weeks later, the grown plants were pulled out without damaging them, and the degree of injury of 10 selected plants was evaluated based on the following ratings to determine a root-knot index:

Degree of injury
 0 = no root-knot formation (perfect control)
 1 = slight root-knot formation
 3 = extensive root-knot formation
 4 = very extensive root-knot formation (corresponding to non-treatment)

$$\text{Root-knot index} = \frac{\Sigma \text{ (rating} \times \text{number of roots)}}{\left[\begin{array}{c}\text{total number of}\\\text{examined roots}\end{array}\right] \times 4} \times 100$$

From above, the following control effect was obtained:

$$\text{Control effect} = \frac{\left[\begin{array}{c}\text{root-knot index of}\\\text{untreated plot}\end{array}\right] - \left[\begin{array}{c}\text{root-knot index}\\\text{of treated plot}\end{array}\right]}{\text{root-knot index of untreated plot}} \times 100$$

A control effect of 100% means a perfect control. The results are shown in Table 7.

TABLE 7

| Compound | Control effect (%) at a concentration of the active ingredient (ppm) of | |
|---|---|---|
| | 50 | 10 |
| (1) | 100 | 100 |
| (2) | 100 | 100 |
| A | 0 | 0 |
| B | 90 | 0 |
| C | 0 | 0 |
| D | 0 | 0 |

It will be appreciated that the instant specification and examples are set forth by way of illustration and not limitation and that various modifications and changes may be made without departing from the spirit and scope of the present invention.

What is claimed is:

1. An O-alkyl-S-alkyl-O-haloalkyl-phosphate of the formula

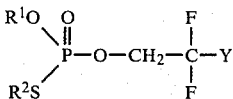

in which
  $R^1$ and $R^2$ each independently is alkyl with 1–4 carbon atoms, and
  Y is halogenoalkyl with 1–4 carbon atoms.

2. A compound according to claim 1 in which $R^1$ is ethyl, $R^2$ is n-propyl and Y is di- or trihalogenomethyl.

3. A compound according to claim 1 in which said compound is O-ethyl-S-n-propyl-O-2,2,3,3-tetrafluoro-1-propylphosphorothiolate of the formula

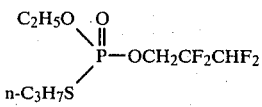

4. A compound according to claim 1 in which said compound is O-ethyl-S-n-propyl-O-2,2,3,3,3-pentafluoro-1-propylphosphorothiolate of the formula

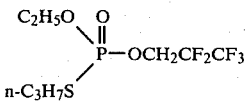

5. An arthropodicidal or nematicidal composition containing as active ingredient an arthropodicidally or nematicidally effective amount of a compound according to claim 1 in admixture with a diluent.

6. An arthropodicidal or nematicidal composition containing as active ingredient an arthropodicidally or nematicidally effective amount of a compound according to claim 3 in admixture with a diluent.

7. An arthropodicidal or nematicidal composition containing as active ingredient an arthropodicidally or nematicidally effective amount of a compound according to claim 4 in admixture with a diluent.

8. A method of combating arthropods or nematodes which comprises applying to the arthropods or nematodes or to a habitat thereof, an arthropodicidally or nematocidally effective amount of a compound according to claim 1.

9. A method of combating arthropods or nematodes which comprises applying to the arthropods or nematodes or to a habitat thereof an arthropodicidally or nematocidally effective amount of a compound according to claim 3.

10. A method of combating arthropods or nematodes which comprises applying to the arthropods or nematodes or to a habitat thereof an arthropodicidally or nematocidally effective amount of a compound according to claim 4.